US010278947B2

(12) United States Patent
Slusarewicz et al.

(10) Patent No.: US 10,278,947 B2
(45) Date of Patent: May 7, 2019

(54) CROSSLINKER ENHANCED REPAIR OF CONNECTIVE TISSUES

(71) Applicant: Orthopeutics, L.P., Lexington, KY (US)

(72) Inventors: Pawel Slusarewicz, Lexington, KY (US); David A. Puleo, Lexington, KY (US); Thomas Paul Hedman, Lexington, KY (US); Sharath C. Sundararaj, Lexington, KY (US)

(73) Assignee: ORTHOPEUTICS, L.P., Lexington, KY (US)

( * ) Notice: Subject to any disclaimer, the term of this patent is extended or adjusted under 35 U.S.C. 154(b) by 526 days.

(21) Appl. No.: 14/178,523

(22) Filed: Feb. 12, 2014

(65) Prior Publication Data

US 2014/0161844 A1    Jun. 12, 2014

Related U.S. Application Data

(60) Continuation-in-part of application No. 13/700,091, filed as application No. PCT/US2011/038155 on May 26, 2011, now abandoned, which is a continuation-in-part of application No. 12/715,737, filed on Mar. 2, 2010, now Pat. No. 8,211,938, which is a division of application No. 11/712,684, filed on Feb. 28, 2007, now Pat. No. 8,022,101, said application No. 13/700,091 is a continuation-in-part of application No. 11/975,072, filed on Oct. 17, 2007, now Pat. No. 8,119,599, which is a continuation-in-part of application No. 11/726,790, filed on Mar. 22, 2007, now abandoned.

(60) Provisional application No. 61/771,248, filed on Mar. 1, 2013, provisional application No. 61/348,977, filed on May 27, 2010.

(51) Int. Cl.
*A61K 31/35*    (2006.01)
*A61K 31/121*    (2006.01)

(52) U.S. Cl.
CPC ........... *A61K 31/35* (2013.01); *A61K 31/121* (2013.01)

(58) Field of Classification Search
None
See application file for complete search history.

(56) References Cited

U.S. PATENT DOCUMENTS

| | | |
|---|---|---|
| 4,201,216 A | 5/1980 | Mattei |
| 4,624,256 A | 11/1986 | Messier et al. |
| 4,705,820 A | 11/1987 | Wang et al. |
| 4,857,602 A | 8/1989 | Casey et al. |
| 5,007,934 A | 4/1991 | Stone |
| 5,100,433 A | 3/1992 | Bezwada et al. |
| 5,108,438 A | 4/1992 | Stone |
| 5,156,956 A | 10/1992 | Motoki et al. |
| 5,158,574 A | 10/1992 | Stone |
| 5,312,642 A | 5/1994 | Chesterfield et al. |
| 5,412,076 A | 5/1995 | Gagnieu |
| 5,543,218 A | 8/1996 | Bennett et al. |
| 5,549,904 A * | 8/1996 | Juergensen ............ A61K 38/45 424/423 |
| 5,681,353 A | 10/1997 | Li et al. |
| 5,716,376 A | 2/1998 | Roby et al. |
| 5,916,573 A | 6/1999 | Spiers et al. |
| 5,939,385 A | 8/1999 | Labroo et al. |
| 5,952,011 A | 9/1999 | O'Hara et al. |
| 6,042,610 A | 3/2000 | Li et al. |
| 6,093,204 A | 7/2000 | Stone |
| 6,106,555 A | 8/2000 | Yang |
| 6,165,489 A | 12/2000 | Berg et al. |
| 6,306,169 B1 | 10/2001 | Lee et al. |
| 6,375,672 B1 | 4/2002 | Aksan et al. |
| 6,545,042 B2 * | 4/2003 | Sung ....................... A61L 15/28 514/456 |
| 6,620,846 B1 | 9/2003 | Jonn et al. |
| 6,632,457 B1 * | 10/2003 | Sawhney ............. A61K 9/1647 424/486 |
| 6,719,797 B1 | 4/2004 | Ferree |

(Continued)

FOREIGN PATENT DOCUMENTS

| | | | |
|---|---|---|---|
| GB | 2384490 | * 7/2003 | ............... C09K 7/02 |
| JP | H0779707 A | 3/1995 | |

(Continued)

OTHER PUBLICATIONS

Di Sabatino et al., Autoimmunity Rev., 11:746-753 (2012).*
Abraham et al.; Evaluation of the porcine intestinal collagen layer as a biomaterial; Journal of Biomedical Materials Research (2000) vol. 51, No. 3, pp. 442-452.
Adams, et al.; 1981 Volvo Award in Basic Science, Prolapsed Intervertebral Disc; Spine, vol. 7, No. 3, pp. 184-191 (1982).
Agrawal, et al.; Technique to control pH in vicinity of biodegrading PLA-PGA implants; Journal of Biomedical Materials Research 1997; 36:105-14.

(Continued)

*Primary Examiner* — Thomas J. Visone
(74) *Attorney, Agent, or Firm* — King & Schickli, PLLC

(57) ABSTRACT

A protein crosslinker delivery device includes a body and a protein crosslinker held in a synthetic or natural biodegradable polymer. The body, a coating on the body, or an attachment to the body can contain the protein crosslinker holding biodegradable polymer. The release rate of the crosslinker and total amount of crosslinker released can be controlled by varying the concentration of the crosslinker and by varying the composition and structural characteristics of the degradable polymer. Surface eroding, bulk eroding and naturally occurring biodegradable polymers can be used in conjunction with a variety of nontoxic or minimally-toxic protein crosslinking agents. The devices can be used to treat mechanically damaged, deformed, and nutritionally deficient connective or soft tissues such as the knee meniscus, the spinal disc, the cornea, ligaments and tendons, the soft palate, and skin.

21 Claims, 2 Drawing Sheets

(56) References Cited

U.S. PATENT DOCUMENTS

| | | | |
|---|---|---|---|
| 6,812,211 | B2 | 11/2004 | Slivka et al. |
| 6,838,493 | B2 | 1/2005 | Williams et al. |
| 7,208,300 | B2 | 4/2007 | Evans et al. |
| 7,388,043 | B2 * | 6/2008 | Errasquin ............... C08F 8/34 523/205 |
| 7,435,722 | B2 | 10/2008 | Hedman |
| 7,563,277 | B2 | 7/2009 | Case et al. |
| 7,919,112 | B2 | 4/2011 | Pathak et al. |
| 8,022,101 | B2 | 9/2011 | Hedman |
| 8,025,696 | B2 | 9/2011 | Osada et al. |
| 8,092,529 | B2 | 1/2012 | Malaviya et al. |
| 8,119,599 | B2 | 2/2012 | Hedman et al. |
| 8,153,600 | B2 | 4/2012 | Hedman |
| 8,198,248 | B2 | 6/2012 | Hedman et al. |
| 8,211,938 | B2 | 7/2012 | Hedman |
| 8,283,322 | B2 | 10/2012 | Slusarewicz et al. |
| 8,450,276 | B2 | 5/2013 | Hedman |
| 2001/0018614 | A1 | 8/2001 | Bianchi |
| 2003/0023190 | A1 | 1/2003 | Cox |
| 2003/0036797 | A1 | 2/2003 | Malaviya et al. |
| 2003/0049301 | A1 | 3/2003 | Hedman |
| 2003/0181365 | A1 | 9/2003 | Slivka et al. |
| 2004/0010048 | A1 | 1/2004 | Evans et al. |
| 2004/0010251 | A1 | 1/2004 | Pitaru et al. |
| 2004/0133275 | A1 | 7/2004 | Mansmann |
| 2004/0170685 | A1* | 9/2004 | Carpenter ............ A61K 31/685 424/468 |
| 2004/0253219 | A1 | 12/2004 | Hedman |
| 2005/0271590 | A1* | 12/2005 | Schwartz ............ A61K 31/135 424/9.5 |
| 2005/0276841 | A1* | 12/2005 | Davis ................. A61K 9/0051 424/443 |
| 2006/0069011 | A1 | 3/2006 | Kusanagi et al. |
| 2006/0286289 | A1 | 12/2006 | Prajapati et al. |
| 2007/0183973 | A1 | 8/2007 | Hedman |
| 2007/0196351 | A1 | 8/2007 | Hedman |
| 2007/0202143 | A1 | 8/2007 | Hedman |
| 2007/0248567 | A1* | 10/2007 | Pathak ............. A61K 47/48215 424/78.27 |
| 2008/0119930 | A1 | 5/2008 | Osada et al. |
| 2008/0260712 | A1 | 10/2008 | Hedman |
| 2009/0062922 | A1 | 3/2009 | Mckay |
| 2010/0040593 | A1 | 2/2010 | Hedman et al. |
| 2010/0040594 | A1 | 2/2010 | Slusarewicz et al. |
| 2010/0041616 | A1 | 2/2010 | Hedman et al. |
| 2010/0158887 | A1 | 6/2010 | Hedman |
| 2011/0060070 | A1 | 3/2011 | Dias |
| 2011/0082199 | A1 | 4/2011 | Hedman |
| 2011/0106243 | A1 | 5/2011 | Van Dongen et al. |
| 2011/0177150 | A1 | 7/2011 | Pathak et al. |
| 2011/0182957 | A1 | 7/2011 | Nicoll et al. |
| 2011/0301525 | A1 | 12/2011 | Nicoll et al. |
| 2013/0085569 | A1 | 4/2013 | Hedman et al. |
| 2013/0087155 | A1 | 4/2013 | Hedman et al. |

FOREIGN PATENT DOCUMENTS

| | | |
|---|---|---|
| WO | 9806830 A1 | 2/1998 |
| WO | 9819718 A1 | 5/1998 |
| WO | 0204739 A1 | 1/2002 |
| WO | 2010001149 A2 | 1/2010 |
| WO | 2011150218 A1 | 12/2011 |

OTHER PUBLICATIONS

Allen, et al.; Late degenerative changes after meniscectomy. Factors affecting the knee after operation; Journal of Bone and Joint Surgery 1984; 66:666-71.

Arnoczky, et al.; Meniscal repair using an exogenous fibrin clot. An experimental study in dogs; Journal of Bone and Joint Surgery 1988; 70:1209-17.

Arnoczky, et al.; Meniscal replacement using a cryopreserved allograft. An experimental study in the dog; Clinical Orthopaedics and Related Research 1990; 121-8.

Athanasiou, et al.; In vitro degradation and release characteristics of biodegradable implants containing trypsin inhibitor; Clinical Orthopaedics and Related Research 1995; 272-81.

Averous, et al.; Biodegradable Polymers; Chapter 2 in Environmental Silicate Nano-Biocomposites, pp. 13-39; Springer 2012.

Hedman, et al.; Quantification of Intervertebral Disc Degradation Resulting from Fatigue, USC Orthopaedic Research Lab; 48th Annual Meeting of the Orthopaedic Research Society, Paper No. 0120. (no date available).

Barber, et al.; Load to failure testing of new meniscal repair devices; Arthroscopy 2004; 20:45-50.

Barber, et al.; Meniscal repair devices; Arthroscopy 2000; 16:613-8.

Board of Patent Appeals and Interferences, Interference No. 105, 653, Document No. 133, Decision on Motions dated Nov. 23, 2010, pp. 1-29.

Bouchard, et al.; Posterior Decompression and in situ Fusion for the Treatment of Degenerative Scoliosis; Orthopaedics and Traumatology, 4 (1995) 54-59.

Boyd-White, et al.; Effect of cross-linking on matrix permeability. A model for AGE-modified basement membranes; Diabetes 1996; 45:348-53.

Buckwalter, et al.; Current Concepts Review, Soft-Tissue Aging and Musculoskeletal Function; Journal of Bone & Joint Surgery, vol. 75-A(10) Oct. 1993, pp. 1533-1548.

Buckwalter; Aging and Degeneration of the Human Interverbral Disc; Spine, 20:1307-4, 1995.

Cammisa; Minimally Invasive Spine Surgery, Hospital for Special Surgery, date posted: Dec. 5, 2003, pp. 1-11.

Chachra, et al.; Effect of applied uniaxial stress on rate and mechanical effects of cross-linking in tissue-derived biomaterials; Biomaterials, 17:1865-75, 1996.

Charulatha, et al.; Influence of different crosslinking treatments on the physical properties of collagen membranes; Biomaterials 2003; 24:759-67.

Hedman, et al.; Exogenous cross-linking increases the stability of spinal motion segments; Spine 2006; 31:480-5.

Chasin, et al; Biodegradable Polymers as Drug Delivery Systems; Drugs and the Pharmaceutical Sciences, vol. 45.; 1990; Marcel Dekker, Inc., New York.

Chen, et al.; Induction of Advanced Glycation End Products and Alterations of the Tensile Properties of Articular Cartilage; Arthritis & Rheumatism, vol. 46, No. 12, pp. 3212-3217 (Dec. 2002).

Chen, et al.; Age-related crosslinking alters tensile properties of articular cartilage; 47th Annual Meeting, Orthopaedic Research Society, p. 128, Feb. 2001.

Chuang, et al., 53rd Annual Meeting of the Orthopaedic Research Society; The Biomechanical Properties and Stability of Lumbar Spinal Motion Segment Following Lumbar Posterior Decompression Surgeries; Cedars-Sinai Institute for Spinal Disorders, LA, CA USA, Poster No. 1025 (no date available).

Chuang, et al.; Effects of exogenous crosslinking on in vitro tensile and compressive moduli of lumbar intervertebral discs; Clinical Biomechanics 2006; pp. 1-7.

Chuang, et al.; The Effects of Exogenous Crosslinking on Hydration and Fluid Flow in the Intervertebral Disc Subjected to Compressive Creep Loading and Unloading; Spine 2010, vol. 35, No. 24, pp. E1362-E1366.

Cook, et al.; A novel bioabsorbable conduit augments healing of avascular meniscal tears in a dog model; American Journal of Sports Medicine 2007; 35:1877-87.

Deutman; The case for chemonucleolysis in discogenic sciatica; Dept. of Orthopeadics, Martino Hospital, Acta Orthopaedic Scandinavica 63(5):571-575 (1992).

Duance, et al.; Changes in collagen cross-linking in degenerative disc disease and scoliosis; Spine, 23:2545-51, 1998.

Jun. 2, 2009 Office Action in U.S. Appl. No. 11/346,464.

Apr. 21, 2009 Office Action in U.S. Appl. No. 11/726,790.

May 22, 2009 Advisory Action in U.S. Appl. No. 11/712,684.

Jul. 16, 2009 Office Action in U.S. Appl. No. 11/712,684.

Fairbank; Knee joint changes after meniscectomy; Journal of Bone and Joint Surgery 1948; 30B:664-70.

Forman, et al.; Laser-assisted fibrin clot soldering of human menisci; Clinical Orthopaedics and Related Research 1995; 37-41.

(56) References Cited

OTHER PUBLICATIONS

Fox, et al.; Trephination of incomplete meniscal tears; Arthroscopy 1993; 9:451-5.
Freedman, et al.; Marrow stimulating technique to augment meniscus repair; Arthroscopy 2003; 19:794-8.
Garrett, et al.; Meniscal transplantation in the human knee: a preliminary report; Arthroscopy 1991; 7:57-62.
Giandomenico, et al.; Retinoic acid and 4-hydroxyphenylretinamide induce growth inhibition and tissue transglutaminase through different signal transduction pathways in mouse fibroblasts (NIH 3T3 cells); Carcinogenesis (1999) vol. 20, No. 6, pp. 1133-1135.
Goel, et al.; Interlaminar Shear Stresses and Laminae Separation in a Disc; Spine. vol. 20, No. 6, 689-98 (1995).
Goel, et al.; Kinematics of the whole lumbar spine. Effect of discectomy; Spine, 10-(6):543-54, 1985.
Goel, et al.; Mechanical properties of lumbar spinal motion segments as affected by partial disc removal; Spine, 11 (10):1008-121986.
Gratzer, et al.; Control of pH alters the type of cross-linking produced by 1-ethyl-3-(3-dimethylaminopropyl)-carbodiimide (EDC) treatment of acellular matrix vascular grafts; pp. 172-179; John Wiley & Sons, Inc. 2001.
Green et al.; Tensile Properties of the annulus fibrosus; European Spine Journal: vol. 2, pp. 209-214 (1993).
Greve, et al.; Collagen crosslinking and cartilage glycosaminoglycan composition in normal and scoliotic chickens; Biochemical et Biophysical Acta, 967:275-283, 1988.
Gunatillake, et al.; Biodegradable Synthetic Polymers for Tissue Engineering; European Cells and Materials vol. 5 (2003), pp. 1-16.
Han, et al.; Proanthocyanidin: a natural crosslinking reagent for stabilizing collagen matrices; Journal of Biomedical Materials Research 2003; 65:118-24.
Hatayama, et al.; Histologic changes after meniscal repair using radiofrequency energy in rabbits; Arthroscopy 2007; 23:299-304.
Fu, et al.; Motion of the knee meniscus during knee flexion; In: Mow VC. Arnoczky SP, Jackson DW, eds. Knee Meniscus: Basic and Clinical Foundations, Chapter 6; New York. NY: Raven Press. 1992; 75-89.
Hennerbichler, et al.; Repair response of the inner and outer regions of the porcine meniscus in vitro; American Journal of Sports Medicine 2007; 35:754-62.
Hoffmann, et al.; Glutaraldehyde and oxidised dextran as crosslinker reagents for chitosan-based scaffolds for cartilage tissue engineering; Journal of Materials Science Materials in Medicine 2009; 20:1495-503.
Horner, et al.; 2001 Volvo Award Winner in basic science studies: Effect of Nutrient Supply on the Viability of Cells from the Nucleus Pulposus of the Intervertebral Disc; Spine (2001), vol. 26, No. 23, pp. 2543-2549.
Hunter et al.; Effects of Matrix Stabilization Using Glutaraldehyde on the Material Properties of Porcine Meniscus; BED American Society of Mechanical Engineers (2001) vol. 50, pp. 787-788.
Hunter, et al.; Meniscal material properties are minimally affected by matrix stabilization using glutaraldehyde and glycation with ribose; Journal of Orthopaedic Research 2005; 23:555-61.
Imakiire, et al.; Experimental study on thermal welding for the knee meniscal white zone; Journal of Orthopaedic Science 2003; 8:683-92.
International Search Report and Written Opinion for International application No. PCT/US11/38155 dated Sep. 16, 2011.
Izuta, et al.; Meniscal repair using bone marrow-derived mesenchymal stem cells: experimental study using green fluorescent protein transgenic rats; Knee. 2005; 12:217-23.
Jakob, et al.; The arthroscopic meniscal repair. Techniques and clinical experience; American Journal of Sports Medicine 1988; 16:137-42.
Jitsuiki, et al.; Meniscal repair enhanced by an interpositional free synovial autograft: an experimental study in rabbits; Arthroscopy 1994; 10:659-66.

Jorgensen, et al.; Long-term follow-up of meniscectomy in athletes. A prospective longitudinal study; Journal of Bone and Joint Surgery 1987; 69:80-3.
Justinger, et al.; "Antibiotic coating of abdominal closure sutures and wound infection"; Surgery 2009, vol. 145, No. 3, pp. 330-334.
Klapperich, et al.; A novel biocompatible adhesive incorporating plant-derived monomers; Journal of Biomedical Materials 2009; 91: 378-84.
Kotilainen et al., Clinical Instability of the Lumbar Spine after Microdiscectomy, Acta Neurochir (Wien) (1993) 125:120-126.
Kotilainen, et al.; Percutaneous nucleotomy in the treatment of lumbar disc herniation results after a mean follow-up of 2 years; Acta Neurochirurgica (Wien), 128(1-4):47-52, 1994.
Kotilainen; Long-Term Outcome of Patients Suffering from Clinical Instability After Microsurgical Treatment of Lumbar Disc Herniation; Acta Neurochirurgica (Wien) (1998) 140:120-125.
Kurniawan, et al.; Formation of Wheat-Protein-Based Biomaterials through Polymer Grafting and Crosslinking Reactions to Introduce New Functional Properties; Macromolecular Bioscience (2009), 9(1):93-101.
Lai; Biocompatibility of chemically cross-linked gelatin hydrogels for ophthalmic use; Journal of Material Science: Materials in Medicine 21, 1899-1911 (2010).
Lee, et al.; The bovine pericardial xenograft: I. Effect of fixation in aldehydes without constraint on the tensile viscoelastic properties of bovine pericardium; Journal of Biomedical Materials Research 1989, vol. 23, pp. 457-475.
Lopez, et al.; The effects of monopolar radiofrequency energy on intact and lacerated ovine menisci; Arthroscopy 2001; 17:613-9.
Mahdavi, et al.; A biodegradable and biocompatible gecko-inspired tissue adhesive; PNAS 2008; vol. 105, pp. 2307-2312.
Middleton, et al.; "Synthetic biodegradable polymers as orthopedic devices"; Biomaterials 2000, vol. 21, pp. 2335-2346.
Sung, et al.; Stability of a biological tissue fixed with a naturally occurring crosslinking agent (genipin); Journal of Biomedical Materials 2001; 55:538-46.
Milachowski, et al.; Homologous meniscus transplantation. Experimental and clinical results; Intl. Orthopaedic. 1989; 13:1-11.
Nair, et al.; "Biodegradable polymers as biomaterials"; Progress in Polymer Science 2007, vol. 32, pp. 762-798.
Nakhostine, et al.; Effects of abrasion therapy on tears in the avascular region of sheep menisci; Arthroscopy 1990; 6:280-7.
Ochi, et al.; Expression of cytokines after meniscal rasping to promote meniscal healing; Arthroscopy 2001; 17:724-31.
Okuda, et al.; Meniscal rasping for repair of meniscal tear in the avascular zone; Arthroscopy 1999; 15:281-6.
Osti, et al.; Annular tears and disc degeneration in the lumbar spine: a post-mortem study of 135 discs; Journal of Bone and Joint Surgery, 74B:678-682, 1992.
Panjabi, et al.; Subfailure Injury of the Rabbit Anterior Cruciate Ligament; Journal of Orthopaedic Research vol. 14, No. 2, pp. 216-222, (1996).
Park, et al.; Characterization of porous collagen/hyaluronic acid scaffold modified by 1-ethyl-3-(3-dimethylaminopropyl) carbodiimide cross-linking; Biomaterials 23, 1205-1212 (2002).
Powers, et al.; Glutaraldehyde-cross-linked meniscal allografts: clinical, gross, and histological results; Journal of Investigative Surgery 1988; 1:249•57.
Proctor, et al.; Material properties of the normal medial bovine meniscus; Journal of Orthopaedic Research 1989; 7:771-82.
Rankin, et al.; A biomechanical analysis of meniscal repair techniques; American Journal of Sports Medicine 2002; 30:492-7.
Rosenberg, et al.; Arthroscopic meniscal repair evaluated with repeat arthroscopy; Arthroscopy 1988; 2:14•20.
Sethi, et al.; Technical tips in orthopedics: meniscal repair with use of an in situ fibrin clot; Arthroscopy 2003; 19:E44.
Sheehan, et al.; Stress Fracture of the Pedicle After Extensive Decompression and Contralateral Posterior Fusion for Lumbar Stenosis; Neurosurgical Focus vol. 13, Aug. 2002, pp. 1-6.
Singhal, et al.; Salient Degradation Features of a 50:50 PLA/PGA Scaffold for Tissue Engineering; Tissue Eng 1996; 2:197-207.

(56) References Cited

OTHER PUBLICATIONS

Slusarewicz, et al.; Kinetic characterization and comparison of various protein crosslinking reagents for matrix modification; Journal of Materials Science Materials in Medicine 2010; 21:1175-81.
Slusarewicz, et al.; Optimization of Protein Crosslinking Formulations for the Treatment of Degenerative Disc Disease; Spine 2010; In Press.
Spoerl et al.; Induction of Cross-Links in Corneal Tissue; Experimental Eye Research (1998) vol. 66, pp. 97-103.
Stone, et al.; Autogenous replacement of the meniscus cartilage: analysis of results and mechanisms of failure; Arthroscopy 1995; 11:395-400.
Stone, et al.; Future directions. Collagen-based prostheses for meniscal regeneration; Clinical Orthopaedics and Related Research 1990; 129-35.
Stone, et al.; Meniscal regeneration with copolymeric collagen scaffolds. In vitro and in vivo studies evaluated clinically, histologically, and biochemically; American Journal of Sports Medicine 1992; 20:104-11.
Stone, et al.; Regeneration of meniscal cartilage with use of a collagen scaffold. Analysis of preliminary data; Journal of Bone and Joint Surgery 1997; 79:1770-7.
Storch, et al.; Experimental efficacy study of coated VICRYL plus antibacterial suture in guinea pigs challenged with *Staphylococcus aureus*; Surgical Infections 2004, vol. 5, No. 3, pp. 281-288.
Sung, et al.; Crosslinking characteristics and mechanical properties of a bovine pericardium fixed with a naturally occurring crosslinking agent; Journal of Biomedical Materials 1999; 47:116-26.
Sung, et al.; Mechanical properties of a porcine aortic valve fixed with a naturally occurring crosslinking agent; Biomaterials 1999; 20:1759-72.
Talley, et al.; Treatment of partial meniscal tears identified during anterior cruciate ligament reconstruction with limited synovial abrasion; Arthroscopy 2000; 16:6-10.
Tang, et al.; Effects of collagen crosslinking on tissue fragility; Clinical Biomechanics (Bristol., Avon.) 2008; 23:122-3.
Teng, et al.; Physical crosslinking modulates sustained drug release from recombinant silk-elastin like protein polymer for ophthalmic applications; Journal of Controlled Release (2011), 156(2): 186-94.
Thompson, et al.; Bone indentation recovery time correlates with bond reforming time; Nature, 414:773-6, 2001.
Tienen, et al.; Replacement of the knee meniscus by a porous polymer implant: a study in dogs; American Journal of Sports Medicine 2006; 34:64-71.
Uggen, et al.; "The Effect of Recombinant Human Platelet-Derived Growth Factor BB-Coated Sutures on Rotator Cuff Healing in a Sheep Model"; Arthroscopy: The Journal of Arthroscopic & Related Surgery (Nov. 2010), vol. 26, No. 11, pp. 1456-1462.
Uhrich, et al.; Polymeric Systems for Controlled Drug Release; Chemical Reviews 1999, vol. 99, No. 11, pp. 3181-3198.
Van Trommel, et al.; Arthroscopic meniscal repair with fibrin clot of complete radial tears of the lateral meniscus in the avascular zone; Arthroscopy 1998; 14:360-5.
Vasudev, et al.; Effect of alternative crosslinking techniques on the enzymatic degradation of bovine pericardia and their calcification; Journal of Biomedical Materials 1997; 35:357-69.
Verzijl, et al.; Crosslinking by advanced glycation end products increases the stiffness of the collagen network in human articular cartilage: a possible mechanism through which age is a risk factor for osteoarthritis; Arthritis and Rheumatism 2002; 46:114-23.

Von Burkersroda, et al.; Why degradable polymers undergo surface erosion or bulk erosion; Biomaterials 23 (2002), pp. 4221-4231.
Wagner, et al.; Glycation increases human annulus fibrosus stiffness in both experimental measurements and theoretical predictions; Journal Biomechanics 2006; 39:1021-9.
Walker, et al.; The role of the menisci in force transmission across the knee; Clinical Orthopaedics and Related Research 1975; 184-92.
Wang, et al.; Changes in the fracture toughness of bone may not be reflected in its mineral density, porosity, and tensile properties; Bone, 23:67-72, 1998.
Wisnewski, et al.; Glutaraldehyde-cross-linked meniscal allografts: mechanical properties; Journal of Investigative Surgery 1988; 1:259-66.
Wu, et al.; Preparation and assessment of glutaraldehyde-crosslinked collagen-chitosan hydrogels for adipose tissue engineering; Journal of Biomedical Materials 2007; 81:59-65.
Wuertz et al.; MSC response to pH levels found in degenerating intervertebral discs; Biochemical and Biophysical Research Communications (2009) vol. 379, pp. 824-829.
Yamasaki, et al.; Meniscal regeneration using tissue engineering with a scaffold derived from a rat meniscus and mesenchymal stromal cells derived from rat bone marrow; Journal of Biomedical Materials 2005; 75:23-30.
Yang, et al.; Tricalcium phosphate and glutaraldehyde crosslinked gelatin incorporating bone morphogenetic protein—a viable scaffold for bone tissue engineering; Journal of Biomedical Materials Research Part B Applied Biomaterials 2005; 74:468-75.
Yerramalli, et al.; The effect of nucleus pulposus crosslinking and glycosaminoglycan degradation on disc mechanical function; Biomechanical Model Mechanobiol 2007; 6:13-20.
Zeeman, et al.; Crosslinking and modification of dermal sheep collagen using 1, 4-butanediol diglycidyl ether; Journal of Biomedical Materials Research; 46(3):424-33, 1999.
Zhai, et al.; Crosslinking of decellularized porcine heat valve matrix by procyanidins; Biomaterials 2006; 27:3684-90.
Zhang, et al.; Trephination and suturing of avascular meniscal tears: a clinical study of the trephination procedure; Arthroscopy 1996; 12:726-31.
Arendt, et al.; Orthopaedic Knowledge Update: Sports Medicine 2; Chapter 28: Knee Biomechanics; Rosemont, IL: American Academy of Orthopaedic Surgeons, 1999; pp. 291-305.
Arendt, et al.; Orthopaedic Knowledge Update: Sports Medicine 2; Chapter 33: Meniscal Injuries; Rosemont, IL: American Academy of Orthopaedic Surgeons, 1999; pp. 349-354.
Levy, et al.; The contribution of the menisci to the stability of the knee; In: Mow VC, Arnoczky SP, Jackson DW, eds. Knee Meniscus: Basic and Clinical Foundations, Chapter 8; New York, NY: Raven Press, 1992; 107-15.
Tsai, C., et al., In vitro evaluation of the genotoxicity of a naturally occurring crosslinking agent (genipin) for biologic tissue fixation, J. Biomed. Mater. Res 52: 58-65 (2000).
Kirking, B., et al., The dose response relationship between intervertebral disc flexion-extension neutral zone metrics and injected genipin concentration, J Appl Biomater Funct Mater, 2013; 11(2): 73-79.
Wang, C., et al., Cytocompatibility study of a natural biomaterial crosslinker—Genipin with therapeutic model cells, Journal of Biomedical Materials Research Part B Applied Biomaterials, vol. 978, Issue 1, Apr. 2011.

\* cited by examiner

CROSSLINKER ENHANCED REPAIR OF CONNECTIVE TISSUES

CROSS-REFERENCE TO RELATED APPLICATIONS

This application claims the benefit of U.S. provisional application Ser. No. 61/771,248 filed on Mar. 1, 2013, and is a continuation-in-part of application Ser. No. 13/700,091, having a § 371(c)(1) date of Dec. 13, 2012, and based upon PCT/US11/38155 having a filing date of May 26, 2011, which is a continuation-in-part of application Ser. No. 12/715,737, filed on Mar. 2, 2010, now U.S. Pat. No. 8,211,938, which is a divisional of application Ser. No. 11/712,684, filed Feb. 28, 2007, now U.S. Pat. No. 8,022,101. U.S. application Ser. No. 13/700,091 is also a continuation-in-part of application Ser. No. 11/975,072, filed Oct. 17, 2007, now U.S. Pat. No. 8,119,599, which is a continuation-in-part of application Ser. No. 11/726,790, filed Mar. 22, 2007. U.S. application Ser. No. 13/700,091 also claims the benefit of Provisional Patent Application No. 61/348,977, filed on May 27, 2010. All of the foregoing applications are incorporated by reference herein.

FIELD OF THE INVENTION

This document relates to protein crosslinking reagents for the surgical repair of injuries and diseases of connective tissues in humans or animals.

RELATED ART

This document relates to a novel device and method for repairing injury and disease of the connective tissues or soft tissues such as the knee meniscus. Other connective and soft tissues that can be repaired by this device include, but are not limited to, the shoulder capsule, tendons, ligaments, the intervertebral disc, the soft palate, the cornea and skin.

The menisci of the knee are a pair of crescent-shaped fibrocartilaginous structures attached to the planar apical surface of the tibia. They contact the outer region of the femoral articular cartilage surface and as such play an important role in both load transmission and in maintaining the stability of the joint.

While 65-75% of the mass of the menisci consists of water, the remaining constituents are primarily proteins, with the most common (75%) being type I collagen. Damage to this tissue is one of the most common causes of knee injury and results in surgery to some 850,000 patients per year in the US. Symptoms of meniscal tears are primarily localized pain and swelling, but in cases where fragments of the damaged meniscus lodge between the articulating surfaces of the joint, catching sensations and (in the worst case) locking of the joint can occur.

The first line of treatment for meniscal tears is non-surgical, e.g. rest, icing, physical therapy and/or non-steroidal anti-inflammatory drug (NSAID) treatment. Surgery is indicated for patients who do not respond to physical therapy, who cannot or are unable to sacrifice the time required for potentially unsuccessful therapy and for those with locked joints.

Surgery is most commonly, but not exclusively, conducted arthroscopically to minimize further damage to the joint and to decrease patient recovery times. Damage to the outer periphery of either meniscus heals more readily than that to the inner portions, due to the lack of vasculature in the inner portion of the meniscus. For this reason, tears of the inner meniscus are usually excised in a procedure known as a partial meniscectomy. In the remaining cases, tears are repaired using either suture or a variety of commercially available fixing devices, such as arrows, darts and tacks, in order to facilitate healing of the tear. These devices are generally constructed using biodegradable polymers, such as poly(lactic acid) or poly(glycolic acid), so that no subsequent surgery is required for their removal.

Although arrows, darts and tacks provide temporary support to the tissue as it heals, they are generally not as strong as sutures. However, because their use results in substantially reduced operating times and risk of complications to the patient, they are increasingly gaining favor.

While the above represents the most common approaches to the treatment of meniscal tears, other therapeutic modalities for meniscal repair can be used or are being explored experimentally. These include: stem cell therapy; trephination from the vascular to avascular region to facilitate greater nutrient flow and promote in-growth of vasculature; micro-fracture of the intercondylar notch which may release growth factors or autologous stem cells to aid in the repair process; thermal welding of the tear; enhancement of fibroblast proliferation using radio frequency (RF) radiation; use of fibrin clots to both provide stimuli for both chemotaxis and proliferation of regenerative cells, sometimes in conjunction with laser soldering; meniscal or synovial rasping to promote healing via the release of growth factors from the tissue; and synovial flap grafting at the repair site to provide vasculature.

In addition, meniscal replacement using both artificial implants and allografts is becoming a treatment option in the case of severe tears where meniscectomy is the only other treatment option. In this respect, the possibility of stabilizing allografts and artificial implants against biodegradation using ex vivo protein crosslinking has been explored. The inventors are, however, unaware of any prior art with regard to cros slinking of the native meniscus in situ.

SUMMARY

In accordance with the purposes and benefits described herein, a protein crosslinker delivery device is provided for treating a connective tissue injury. That device is broadly described as comprising a body and a protein crosslinker held in a synthetic or natural biodegradable polymer. For the purposes of this application, a biodegradable polymer is a polymeric material that degrades by any mechanism. Such degradation is generally grouped into polymers that degrade primarily by surface erosion or primarily by bulk erosion. The tendency toward surface or bulk erosion is not exclusive for a material and many polymers undergo a combination of both. For the purposes of this application, a surface erodible polymer refers to a polymer that primarily degrades in vivo from the external surface in a layer by layer manner with minimal water penetration. This degradation occurs within days or hours with the material undergoing chemical hydrolysis or dissolution. For purposes of this application, a bulk erodible polymer refers to a polymer that primarily degrades in vivo throughout the whole volume of the polymer with high water penetration. This degradation occurs within hours to months by the material undergoing chemical hydrolysis. Both surface eroding and bulk eroding polymers have been included under the common terms "biodegradable polymer" or "erodible polymers" in this application. The surface erodible polymer may be selected from a group of polymers consisting of polyanhydrides, poly(ortho esters), association polymers consisting of cellulose acetate phthalate and Pluronic, poly(trimethylene carbonate), polyvinyl alcohol, alginate, maltodextrins, hydroxypropylmethylcellulose, carboxymethylcellulose, polyvinylpyrrolidone, and mixtures thereof. The bulk erodible polymer may be selected from a group of polymers comprising poly(lactic acid) (PLA), poly(glycolic acid) (PGA), copolymers of PLA and PGA (PLGA), polydioxanone, poly(propylene fumarate), polycaprolactone, poly($\beta$-amino ester) hydrogels and mixtures thereof. The biodegradable polymers could also be selected from naturally occurring polymers comprising alginate, dextran, chitosan, hyaluronic acid, cyclodextrin, collagen and mixtures thereof. Further, the protein crosslinker is selected from a group of crosslinkers consisting of genipin (GP), methylglyoxal (MG), proanthrocyanidin (PA), 1-ethyl-3-(3-dimethylaminopropyl) carbodiimide (EDC), L- or D-threose, transglutaminase and mixtures thereof.

One useful embodiment the device further includes a basic salt to neutralize acidic byproducts generated during degradation of the polymer. That basic salt may be selected from a group of salts consisting of calcium carbonate, calcium hydroxyapatite, sodium bicarbonate, 2-amino-2-hydroxymethyl-prysane-1,3-diol(tris), 4-(2-hydroxyethyl)-1-piperazineethanesulfonic acid (HEPES) and mixtures thereof.

In yet another useful embodiment, the body is made of a biodegradable polymer with the crosslinking agent embedded throughout its volume. In still another useful embodiment, the body is made up of a biodegradable polymer with or without a crosslinking agent embedded in it with a coating of the protein crosslinker held in the same or a different biodegradable polymer. In a related embodiment, a nondegradable material without crosslinking agent is coated by a protein crosslinker held in a biodegradable polymer. In a related embodiment, the body is a suture made of collagen (plain or chromic) and is coated by a protein crosslinker held in a biodegradable polymer.

In one possible embodiment, the biodegradable polymer fully degrades within 240 hours. In another possible embodiment, the biodegradable polymer fully degrades within 72 hours. In still another possible embodiment, the biodegradable polymer fully degrades within 48 hours. In yet another possible embodiment the biodegradable polymer fully degrades within 24 hours. In still another possible embodiment the biodegradable polymer fully degrades within 10 hours.

In one possible embodiment, the device is a patch. In another possible embodiment the device is an arrow. In yet another possible embodiment, the device is a dart. In still another possible embodiment, the device is a tack. Still further, in another possible embodiment, the device is a suture. In any of the possible embodiments, the body may include an attachment made from the protein crosslinker held in a biodegradable polymer.

In another embodiment, the device is fabricated from a metal, such as stainless steel or a titanium alloy, in the form of, for example, a staple, pin or wire, and is coated with a biodegradable polymer containing a crosslinking agent.

In another embodiment, the device is an in situ polymerizable injectable formulation containing biodegradable polymer and crosslinking agent in the appropriate solvent. These crosslinker-containing biodegradable polymer solutions would precipitate on injection in vivo and form a temporary layer/filling/scaffold of the biodegradable polymer with crosslinker embedded in it.

In another embodiment, the device is fabricated in the form of biodegradable polymer particles in a suspension with the particles encapsulating a crosslinking agent. These microspheres/microparticles in a suspension can be injected at the appropriate site for release of protein cros slinking agents. The particles can be kept dispersed within the fluid medium by mechanical (fluid movement), electrochemical or chemical factors. In still another useful embodiment, the device is fabricated in the form of nanoscale delivery systems such as liposomes encapsulating a protein crosslinking agent for rapid release. The liposomes can be with or without surface ligands for attaching the liposome to the tissue that is targeted for the cros slinking treatment.

In another embodiment the protein crosslinking agent is embedded in, or coated onto a hard contact lens and used for treatment of the cornea or sclera of the eye. As one example, in the case of astigmatism, the hard contact lens molds or helps in constraining the cornea to an appropriate shape, and the released crosslinking agent fixes the cornea in the constrained shape after removal of the lens.

In accordance with yet another aspect, a method is provided for treating an injury to a connective tissue of a patient. That method comprises contacting the injured connective tissue with a protein crosslinker delivery device as described herein.

These and other embodiments of the device and method will be set forth in the description which follows, and in part will become apparent to those of ordinary skill in the art by reference to the following description and referenced drawing figures.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
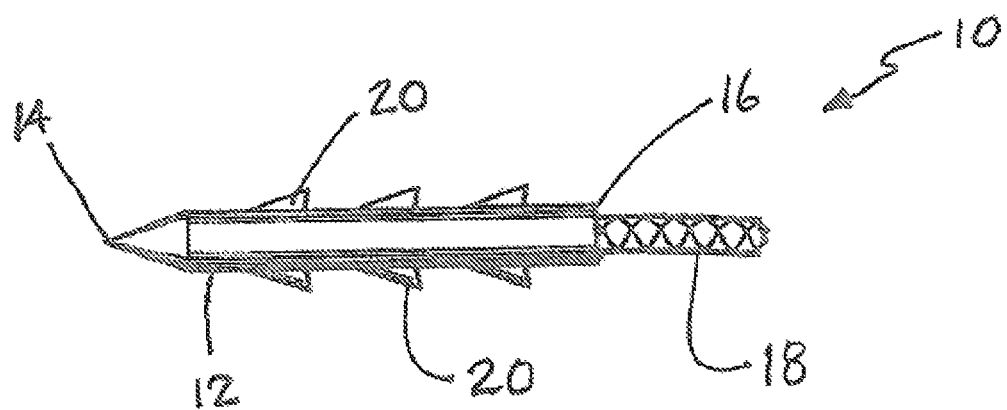
FIG. 1 is a side elevational view of a protein crosslinker delivery device in the form of a dart connected to a suture.

Reference is made to FIG. 1 illustrating a protein crosslinker delivery device 10 in the form of a dart. The device 10 includes a body 12 including a distal end having a pointed tip 14 and a proximal end 16 having a bore or other means for attaching to a suture 18. The body 12 also includes barbs 20 which permit distal movement of the device 10 through body tissue while resisting proximal withdrawal. The body 12 is made from a biodegradable or non-biodegradable polymer with or without embedded crosslinkers coated with a protein crosslinker held in a surface erodible or bulk erodible polymer. In one useful embodiment, the erodible polymer fully erodes within 240 hours. In one useful embodiment, the erodible polymer fully erodes within 72 hours. In another useful embodiment, the erodible polymer fully erodes within 48 hours. In yet another useful embodiment, the erodible polymer fully erodes within 24 hours. In still another useful embodiment, the erodible polymer fully erodes within 10 hours.

Depending on the molecular weight/chain length of the polymer, the surrounding environment (acidic or alkaline) and the geometric dimensions, the surface eroding or bulk eroding polymers might undergo degradation over a time period ranging from days to months. As the polymer degrades, it releases crosslinkers that were held therein. Those therapeutic crosslinkers provide mechanical stabilization for, and increased nutrient flow to, the damaged or torn meniscus tissue.

The surface erodible polymers used in the device 10 include but are not limited to polyanhydrides, poly(ortho esters), association polymers consisting of cellulose acetate phthalate and Pluronic (, poly(trimethylene carbonate), polyvinyl alcohol (PVA), alginate, maltodextrins, hydroxypropylmethylcellulose, carboxymethylcellulose, polyvinylpyrolidone, and mixtures thereof. The bulk erosion polymers used in the device 10 include but are not limited to poly(lactic acid) (PLA), poly(glycolic acid) (PGA), copolymers of PLA and PGA (PLGA), polydioxanone, poly(propylene fumarate), polycaprolactone, poly(β-amino ester) hydrogels and mixtures thereof. The naturally occurring polymers used in the device 10 include but are not limited to alginate, dextran, chitosan, hyaluronic acid, cyclodextrin, collagen and mixtures thereof. Therapeutic protein crosslinkers used in the device 10 include but are not limited to genipin (GP), methylglyoxal (MG), proanthrocyanidin (PA), 1-ethyl-3-(3-dimethylaminopropyl) carbodiimide (EDC), L- or D-threose, transglutaminase and mixtures thereof.

Figure 2:
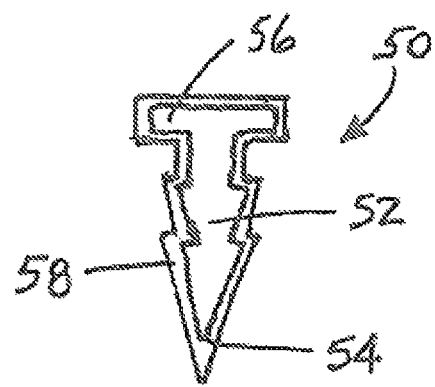
FIG. 2 is a cross sectional view of a protein crosslinker delivery device in the form of a tack.

Reference is now made to FIG. 2, which illustrates a protein crosslinker delivery device 50 in the form of a tack. The device 50 includes a body 52 having a pointed end 54 and a head 56. As illustrated, the body 52 includes a coating 58. The body 52 may be made from a biocompatible material with or without crosslinkers while the coating may be made from a biodegradable polymer containing crosslinkers.

In one possible FIG. 2 embodiment, the body 52 is made from a biocompatible material that is nonabsorbable and thus forms a permanent implant. Such a polymer material may include but is not limited to polyvinylacetate, polyvinylchloride, polypropylene, polyetheretherketone (PEEK), polysulfone, polyethersulfone, polytetrafluoroethylene, polyethylene, polyurethane, polyetherimide and polycarbonate. Such a body 52 may or may not include pores or other surfaces or porous coatings or attached filaments or other attachments for receiving and holding the coating 58 including the biodegradable polymer and crosslinkers. In another embodiment, the device is made from a biocompatible metal, such as (but not limited to) stainless steel, titanium, tantalum, titanium alloys and cobalt alloys. Metal devices may also include pores or additional porous coatings or other surfaces or attachments for receiving and holding the coating containing the biodegradable polymer and crosslinkers.

In an alternative FIG. 2 embodiment, the body 52 is made from a biodegradable polymer, such as poly(lactic acid) or poly(glycolic acid). As noted above, such polymers degrade over the course of weeks or months. Thus, they can remain in place in the body 52 for an extended period of time to provide added support for the injured knee meniscus. Where the biodegradable polymer includes or incorporates therapeutic crosslinkers, the body provides further release of those therapeutic crosslinkers over an extended period of time compared to the crosslinkers that are rapidly released from the erodible coating 58 on the body.

In any of the embodiments, the therapeutic crosslinkers released from the device 10, 50 enter into, and react with, the tissue to form crosslink bonds including covalent bonds. These bonds serve to both strengthen the tissue against further and/or future tearing and also increase the permeability of the tissue to nutrients from the blood supply, thereby enhancing the natural healing process. In addition, and in the case of the knee meniscus, the increase in tissue permeability conferred by the crosslinking will increase the proportion of meniscal tear patients who can be treated surgically since healing using current methods can only occur in regions with sufficient vascular nutrient supply.

While a dart and a tack are illustrated in FIGS. 1 and 2, it should be appreciated that the device can take a number of other forms including, for example, a patch, an arrow or even a suture as illustrated at 18 in FIG. 1.

A method of treating an injury to a knee meniscus of a patient involves contacting the injured area of the meniscus with the device 10, 50. For example, if the device is in the form of a patch 100 (see FIG. 3), it may be attached to the meniscus tissue M using fixation devices, such as arrows, darts, tacks or sutures. Alternatively, the patch 100 may be attached using a suitable biocompatible adhesive. Non-limiting examples of suitable adhesives include poly(glycerol-co-sebacate acrylate), oleic methyl esters or alkyl ester cyanoacrylates.

Solid or liquid crosslinker may be incorporated into the device 10, 50, 100 by addition to the molten polymer prior to casting, molding or spinning. Alternatively the crosslinker may be co-solubilized with the polymer in a suitable solvent (for example, acetone, N-methylpyrrolidone, dimethyl sulfoxide or solvent mixture and then incorporated into the device 10, 50, 100 by removal of the solvent by evaporation or by precipitation (for example, by the addition of ethanol) of the polymer as described previously. The crosslinker and polymer may also be solubilized separately and mixed prior to precipitation in either the same solvent or different (miscible) solvents. Also, the solid crosslinker may also be mixed into the polymer gum formed by precipitation of solubilised polymer prior to molding. The rate of crosslinker release can be controlled by varying the amount or concentration of the crosslinker incorporated into the device as well as by selecting polymers or other materials with differing in vivo degradation rates, and by varying the concentrations or molecular weight/chain length of the polymers.

Alternatively, the crosslinker may be co-solubilized with the polymer in a suitable solvent, solubilized separately in the same solvent and then mixed, or solubilized separately in different miscible solvents and then mixed, and a pre-formed fixation device immersed in this solution. Following removal of the fixation device and evaporation of the solvent, a fixation device containing an outer layer of erodible and/or biodegradable polymer-embedded crosslinker will be produced. The polymer in the outer layer may be different from that of the underlying device both in chain length and/or composition and may be varied, for example, in order to provide different release rates of crosslinker as needed. Additionally, the rate, duration and extent of crosslinker release can be controlled by varying the amount or concentration of the crosslinker incorporated into solvent solution (and therefore the outer layer of the device), by sequential dipping/drying of the fixation device into the crosslinker/polymer/solvent mixture to produce different thicknesses of crosslinker containing polymer at the surface of the device, or by changing the type of polymer or the molecular weight of the polymer used in the coating. Additionally, several crosslinker impregnated outer layers may be used with varying crosslinker amount or concentration and polymer compositions such that the rate of release of crosslinker can be varied as desired. For instance, an initial high rate of crosslinker release can be followed by a low rate of crosslinker release for an extended length of time.

Additionally, in cases where the crosslinker is insufficiently soluble in the solvent used to solubilize the polymer to attain the desired concentration in the final device, additional cosolvents may be added to increase the concentration of the crosslinker. This cosolvent can be less volatile than the solvent used to solubilize the polymer. For example, possible cosolvents used to solubilize the crosslinker genipin in acetone for incorporation into a PLGA coating include, but are not limited to, dimethyl sulfoxide, dimethyl formamide and N-methylpyrrolidone.

Furthermore, in the case of sutures, one or more plasticizers may be added to the coating solution in order to maintain the flexibility of the coating layer and so prevent its cracking and flaking during use. Non-limiting examples of suitable plasticizers are polyethylene glycol (PEG), tributyl citrate, triethyl citrate, glycerine, diethyl phthalate, dibutyl sebacate, triacetin, acetyl tributyl citrate.

It has been previously shown that many crosslinking reagents act less efficiently at low pH. In addition, some biodegradable polymers, including poly(lactic acid) and poly(glycolic acid), degrade to form acidic compounds. In fact, tissue acidification during polymer breakdown has been a concern previously, and incorporation of basic inorganic salts into the polymer matrix has been shown to be effective in maintaining an elevated pH.

In some embodiments, in cases where low-pH sensitive crosslinkers (for example, genipin, methylglyoxal) are used in conjunction with polymers that degrade to form acidic compounds, for example poly(lactic acid) and/or poly(glycolic acid), basic salts are also incorporated as solid suspensions into the erodible polymer matrix. Such salts could be inorganic (for example, but not limited to, calcium carbonate, calcium hydroxyapatite or sodium bicarbonate) or organic (for example, but not limited to, 2-amino-2-hydroxymethyl-propane-1,3-diol (Tris) or 4-(2-hydroxyethyl)-1-piperazineethanesulfonic acid (HEPES).

In some embodiments, the crosslinker is impregnated by one of the methods described above into a flat, biodegradable polymer patch 100. The patch 100 could contain pH conditioning agents and multiple layers of crosslinking agents as described above. The patch 100 (which could be rolled up and inserted via a catheter) is laid over the repaired tissue such that crosslinker is delivered to the meniscus as the patch dissolves and while the patch offers some physical protection to the damaged meniscal tissue as it heals. The surface of the patch opposite to the meniscus additionally provides a smooth bearing surface to the articular cartilage of the femur. Such crosslinker eluting patches can also be applied to other connective tissues of the body, such as the shoulder capsule or the plantar fascia of the foot.

A large number of protein crosslinkers could be used in conjunction with the present invention. In particular embodiments, the crosslinker may be a single crosslinker or a combination of two or more crosslinkers. It has been shown that the conditions that confer optimal reactivity of such crosslinkers differ between reagents and that in some cases other chemicals can enhance their reactivity. In addition, some detergents can also enhance the penetration of crosslinkers through collagenous tissues and therefore help to enhance their ability to crosslink the tissue. Thus, some embodiments may include a chemical or detergent, or any combination thereof that enhances the crosslinking ability of the crosslinker.

Figure 3:
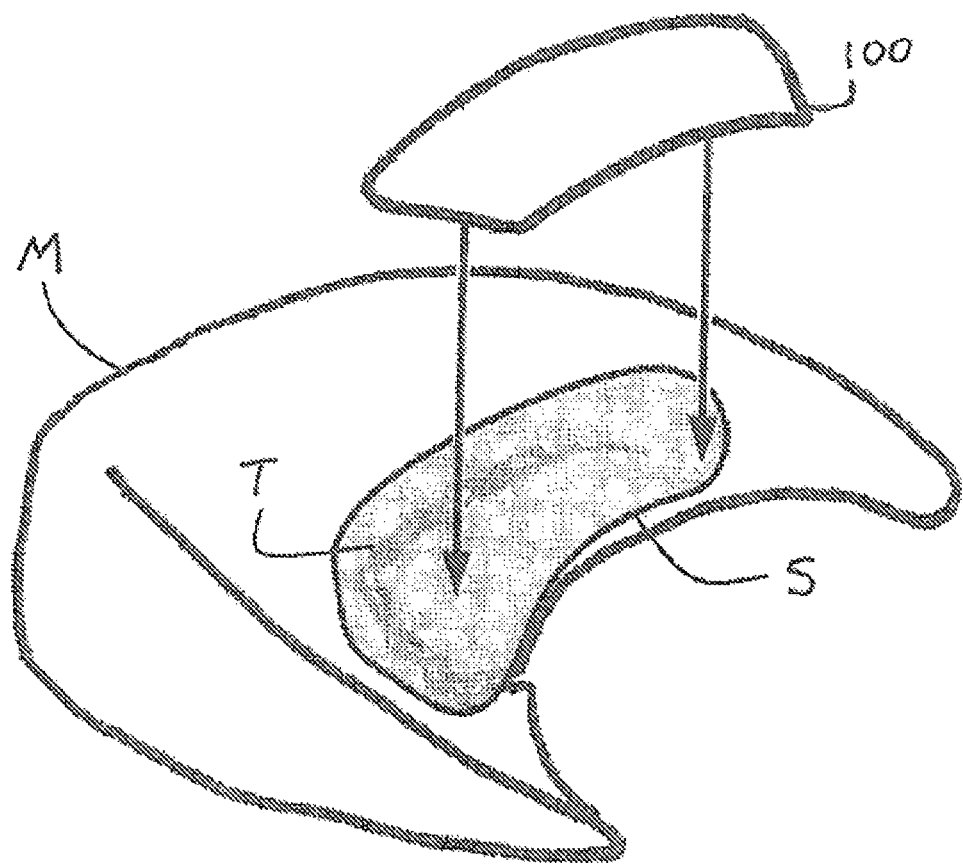
FIG. 3 illustrates a patch and the placement of the patch on an injured meniscus.

Referring to FIG. 3, a stylized human knee meniscus M with a "parrot beak" type tear T is depicted. Following surgical repair, a patch 100 of crosslinker-impregnated material is placed over the damaged tissue. The shaded area 5 depicts the position of the patch 100 following attachment. The patch 100 may be coated with an erodible polymer containing crosslinker. The patch 100 may additionally be attached using typical surgical fixation devices or by addition of a suitable biocompatible solvent or adhesive to the side of the patch 100 in contact with the meniscus. Over time crosslinker will diffuse out of the patch 100 and/or the erodible polymer coating on the patch 100 and into the tissue, both strengthening it and facilitating the diffusion of nutrients into the damaged area by increasing the tissue permeability.

While application of the device 10, 50, 100 to the repair of a diseased or damaged meniscus is described and illustrated in detail above, it should be appreciated that the device 10, 50, 100 and method are generally applicable to the repair of diseased or injured connective tissue in both man and animal. For example, an annulus fibrosis fixation device (suture, tack, etc.) with a crosslinker-releasing coating may be used subsequent to discectomy, nucleus implant surgery, or disc herniation to repair the annulus. Also, these same types of devices may have utility in repair of the shoulder capsular tissues, ankle syndesmosis, Achilles tendon, plantar fascia, carpal tunnel sheath (flexor retinaculum), etc. In another possible example, a coating of erodible polymer and crosslinker could be provided on a device for the soft palate such as a Pillar implant or a synthetic or naturally occurring biodegradable or nondegradable suture.

The present invention may be better understood by referring to the accompanying examples, which are intended for illustration purposes only and should not in any sense be construed as limiting the scope of the invention.

EXAMPLE 1

A patch constructed of a biodegradable polymer, such as poly(lactic acid) (PLA), poly(glycolic acid) (PGA) or poly(lactic-co-glycolic acid) (PLGA) is dip-coated with an aqueous solution containing 10% polyvinyl alcohol (PVA) and 100 mM of the crosslinker methylglyoxal (MG) and then allowed to dry at room temperature. The thickness of the MG-impregnated coating can be varied utilizing multiple applications of solution, by varying the concentration (and thus viscosity) of the PVA polymer, or adjusting the rate at which the patch is withdrawn from the PVA-MG solution. The release rate of the MG can be varied by changing the concentration of the PVA polymer and/or that of the MG.

EXAMPLE 2

A patch constructed of a biodegradable polymer, such as PLA, PGA or PLGA, is sprayed with a solution of partially hydrolyzed PVA in ethanol containing 200 mM of the crosslinker genipin (GP) and allowed to dry. The thickness of the GP-impregnated coating can be varied utilizing multiple applications of solution. The release rate or loading of the GP can be varied by varying the concentration PVA and/or GP in the coating solution. These patches can be used for treatment of meniscal repair as shown in FIG. 3.

EXAMPLE 3

A biodegradable meniscal fixation device, such as a tack or dart, is dip-coated with a solution of 15% association polymer composed of cellulose acetate phthalate (CAP) and Pluronic (P)(CAPP) in acetone containing 400 mM GP and allowed to dry. The total crosslinker loading can be controlled by either varying the concentration of the crosslinker in the coating solution or by the application of numerous sequential coatings. The release rate of the crosslinker can also be changed by varying the ratio of CAP:Pluronic or by varying the concentration of CAPP, plasticizer, and/or GP in the coating solution.

EXAMPLE 4

A PGA suture is dip-coated with a solution of 15% association polymer system (CAPP) in acetone containing 400 mM GP and a plasticizer (such as 3% diethyl phthalate or 5% triethyl citrate or tributyl citrate) and allowed to dry. The total crosslinker loading can be controlled by either varying the concentration of the crosslinker in the coating solution or by the application of multiple coatings. The release rate of the crosslinker can also be changed by varying the ratio of CAP:Pluronic or by varying the concentration of CAPP, plasticizer, and/or GP in the coating solution. The PGA sutures coated with a CAPP layer capable of releasing cross linking agent at appropriate dose and desired rate can be used for meniscal repair.

EXAMPLE 5

A PGA suture is dip coated in a polymer solution consisting of 10% PLGA in cosolvent of DMSO/NMP/acetone with 400-3000 mM GP with 1% to 3% plasticizer, such as PEG. The total crosslinker loading can be controlled by either varying the concentration of the crosslinker in the coating solution or by the application of multiple coatings. The release rate of the crosslinker can also be changed by varying the molecular weight of PLGA or the ratio of lactic to glycolic acid in the PLGA copolymer. The PGA sutures coated with a polymer layer capable of releasing crosslinking agent at appropriate dose and desired rate can be used to increase tear resistance of the tissue and thereby avoid wound dehiscence due to suture pull out.

EXAMPLE 6

A polydioxone suture is dip-coated in a polymer solution consisting of 10% PLGA in cosolvent of DMSO/NMP/acetone with 400-3000 mM GP with 1% to 3% plasticizer, such as PEG. The total crosslinker loading can be controlled by either varying the concentration of the crosslinker in the coating solution or by the application of multiple coatings. The release rate of the crosslinker can also be changed by varying the molecular weight of PLGA or the ratio of lactic to glycolic acid in the PLGA copolymer. These polydioxone sutures coated with a polymer layer capable of releasing crosslinking agent at appropriate dose and desired rate can be used to avoid suture pull out from fibrous tissues such as tendons and ligaments.

EXAMPLE 7

Metal wires and staples dip-coated in a polymer solution consisting of 10% PLGA in cosolvent of DMSO/NMP/acetone with 400-3000 mM GP with 1% to 3% plasticizer, such as PEG. The total crosslinker loading can be controlled by either varying the concentration of the crosslinker in the coating solution or by the application of multiple coatings. The release rate of the crosslinker can also be changed by varying the molecular weight of PLGA or the ratio of lactic to glycolic acid in the PLGA copolymer.

EXAMPLE 8

Non-absorbable sutures, such as polypropylene and nylon, are dip-coated in a polymer solution consisting of 10% PLGA in cosolvent of DMSO/NMP/acetone with 400-3000 mM GP with 1% to 3% plasticizer, such as PEG. The total crosslinker loading can be controlled by either varying the concentration of the crosslinker in the coating solution or by the application of multiple coatings. The release rate of the crosslinker can also be varied by varying the molecular weight of PLGA or the ratio of lactic to glycolic acid in the PLGA copolymer.

Figure 4:
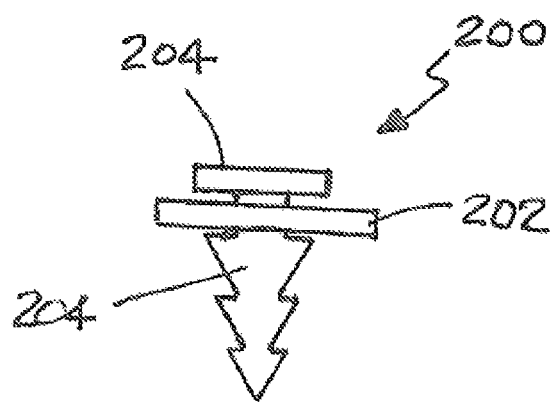
FIG. 4 illustrates another embodiment of a protein crosslinker delivery device including an attachment made from a protein crosslinker held in a biodegradable polymer.

The foregoing examples have been presented for purposes of illustration and description. They are not intended to be exhaustive or to limit the embodiments to the precise forms disclosed. Obvious modifications and variations are possible in light of the above teachings. For example, FIG. 4 illustrates a device 200 in the form of a tack including an attachment 202 made from a protein crosslinker held in an erodible polymer. Here, the term attachment should be broadly interpreted to read upon substantially any form of attachment or cover connected to the body 204 of the device 200. Further, it should be appreciated that the device itself or any coating or attachment to the device may be made from a protein crosslinker and a mixture of erodible and biodegradable polymers in a ratio to achieve a desired crosslinker release rate. All such modifications and variations are within the scope of the appended claims when interpreted in accordance with the breadth to which they are fairly, legally and equitably entitled.

What is claimed:

1. A biocompatible fabricated protein crosslinker delivery device for treating a connective tissue or soft tissue injury in vivo with an animal or human, comprising:
a biocompatible body, wherein the biocompatible body is comprised of a synthetic polymer or a metal and is selected from the group consisting of a patch, an arrow, a dart, a tack, a suture and a staple; and
a dry biodegradable polymer dip coated on to the biocompatible body, wherein the biodegradable polymer comprises a copolymer of poly(lactic acid) and poly(glycolic acid) (PLGA) encapsulating genipin and a plasticizer, wherein degradation of the biodegradable polymer allows for release of genipin in vivo.

2. The device of claim 1, further including a basic salt.

3. The device of claim 2, wherein said basic salt is selected from a group of salts consisting of calcium carbonate, calcium hydroxyapatite, sodium bicarbonate, 2-amino-2-hydroxymethyl-prysane-1,3-diol(tris), 4-(2-hydroxyethyl)-1-piperazineethanesulfonic acid (HEPES) and mixtures thereof.

4. The device of claim 1, wherein said body is porous.

5. The device of claim 1, wherein said biodegradable polymer fully erodes within 240 hours.

6. The device of claim 1, wherein said biodegradable polymer fully erodes within 72 hours.

7. The device of claim 1, wherein said biodegradable polymer fully erodes within 48 hours.

8. The device of claim 1, wherein said biodegradable polymer fully erodes within 24 hours.

9. The device of claim 1, wherein said biodegradable polymer fully erodes within 10 hours.

10. A method of treating an injury to a connective tissue or soft tissue of a patient, comprising:
contacting said injured connective tissue or soft tissue with a protein crosslinker delivery device as set forth in claim 1.

11. The device of claim 1, wherein the plasticizer is polyethylene glycol (PEG).

12. The device of claim 1, wherein the biocompatible body is non-adsorbable.

13. The device of claim 1, wherein the biocompatible body is biodegradable.

14. The device of claim 1, wherein the biocompatible body comprises poly(glycolic) acid.

15. The device of claim 1, wherein the biocompatible body comprises polydioxone.

16. The device of claim 1, wherein the biocompatible body comprises polypropylene.

17. The device of claim 1, wherein the biocompatible body comprises nylon.

18. The device of claim 1, further comprising an outer layer of biodegradable polymer-embedded crosslinker.

19. The device of claim 18, wherein the outer layer biodegradable polymer is different from the biodegradable polymer dip coated on to the biocompatible body.

20. The device of claim 1, wherein the biocompatible body comprises a polymer material selected from the group consisting of polyvinylacetate, polyvinylchloride, polypropylene, polyetheretherketone (PEEK), polysulfone, polyethersulfone, polytetrafluoroethylene, polyethylene, polyurethane, polyetherimide and polycarbonate.

21. The device of claim 1, wherein the biocompatible body comprises a biocompatible metal selected from the group consisting of stainless steel, titanium, tantalum, titanium alloys and cobalt alloys.

* * * * *